United States Patent [19]

Isshiki

[11] Patent Number: 5,106,657

[45] Date of Patent: Apr. 21, 1992

[54] ANIMAL FIBER FOR USE AS WADDING

[76] Inventor: Tadao Isshiki, 8-12, Honjoh 3-chome, Yakeyama, Kure-shi, Japan

[21] Appl. No.: 580,681

[22] Filed: Sep. 11, 1990

[30] Foreign Application Priority Data

Sep. 14, 1989 [JP] Japan .................................. 1-239597

[51] Int. Cl.$^5$ ........................ D02G 3/00; D06M 19/00
[52] U.S. Cl. .................................... 428/375; 8/94.1 R; 8/115.6; 8/127.5; 8/128.1; 428/361; 428/372; 428/378; 428/389
[58] Field of Search ............... 8/94.1 R, 115.52, 115.6, 8/625, 626, 127.5, 128.1; 428/375, 378, 384

[56] References Cited

U.S. PATENT DOCUMENTS

| | | | |
|---|---|---|---|
| 2,805,914 | 9/1957 | Frederick et al. | 8/941.1 R |
| 4,160,051 | 7/1979 | Benisek | 427/352 |
| 4,537,594 | 8/1985 | Fleet et al. | 8/94.1 R |
| 4,680,822 | 7/1987 | Fujino et al. | 5/421 |
| 4,764,173 | 8/1988 | Isshiki | 8/115.2 |
| 4,980,940 | 1/1991 | Isshiki | 5/468 |
| 4,999,243 | 3/1991 | Maeda | 428/372 |

FOREIGN PATENT DOCUMENTS 64-70138 3/1989 Japan .

Primary Examiner—George F. Lesmes
Assistant Examiner—Christopher Brown
Attorney, Agent, or Firm—Armstrong, Nikaido, Marmelstein, Kubovcik and Murray

[57] ABSTRACT

The present invention relates to animal fiber for use as wadding characterized in that a far infrared radiating substance is affixed to the animal fiber together with a water repellent agent. The animal fiber for use as wadding of the present invention has a voluminous and comfortable feeling, suppresses decomposition of proteins such as beta-keratin, prevents a foul odor inherent in such proteins and has an excellent durability. Further, it is capable of enhancing health as well as therapeutic treatment though an effect of far infrared rays.

6 Claims, 1 Drawing Sheet

ANIMAL FIBER FOR USE AS WADDING

BACKGROUND OF THE INVENTION

1. Field of the Invention

The present invention relates to an animal fiber as a filler of wadding used for beddings, cushions, clothes etc., and in particular to an animal fiber having a voluminous and comfortable feeling, suppressing decomposition of proteins such as beta-keratin and preventing a foul smell inherent in such protein and having an excellent durability, and, at the same time, being capable of enhancement of health as well as therapeutic treatment through an effect of far infrared ray.

2. Description of the Prior Art

Animal fibers such as feathers and wool have lately used widely as wadding for high quality beddings for their excellent warmth-keeping performance, lightness and comfortable feeling.

Such animal fibers, which contain as major components proteins such as keratin, have a defect of decreasing in bulkiness with the lapse of time in use, this resulting in decreased bulkiness and an increased foul smell inherent in proteins due to decreased air permeability. In order to avoid such phenomenon it is essential to keep the required bulkiness to ensure good air permeability.

Such animal fibers are generally treated with a large amount of surfactants for the purpose of deodoration and degreasing, but the use of surfactants injures animal fibers to lower their durability, and also causes a decrease of slidability due to degreasing as well as reducing restoration of the voluminous feeling, these resulting in air permeability of animal fibers. Reduced air permeability of animal fibers gives rise to a foul smell as mentioned above, at the same time resulting in massing for further loss of bulkiness and an increase of the degree of the foul smell in a vicious circle. Feather, from its form and structure in particular, has a behavior to move in one direction to be massed in a corner of quilted squares or narrowed portions.

An animal fiber degreased with a surfactant is, so called, in a state of its surface protective layer being stripped off, hence it is decomposed by an alkali contained in sweat during sleep and is crumbled into decay for early loss of bulkiness and deterioration of the comfortable feel as well as the durability.

To sum up, animal fibers for use as wadding such as feathers involve numerous problems in respect of bulkiness, feel as well as durability caused by oil and fat components as a protective layer being removed by the surfactant.

Meanwhile, lately, the effects of far infrared rays of enhancing blood circulation and restoration from fatigue, relieving neuralgia and muscle pain and reactivating the function of stomach and bowels etc. have been made clear and in the field of bedding, too, those utilizing far infrared rays have been proposed.

In Japanese Laid-Open Utility Model 46159/88, for instance, a proposal is made for flexible and permeable quilting provided with a plurality of flat strips as far infrared heaters with an electric circuit controller and wadded with cotton, wool or feather.

A wadded quilt in such a structure, however, has a number of disadvantages as follows;

(1) The structure is complicated and expensive.

(2) The use of the flat strips gives rise to a feeling of physical disorder and loss of soft touch as well as comfortable feeling, this interfering with comfortable sleeping in bed.

(3) The flat strips interfere with the quilt's hygroscopicity of moisture and sweat as well as its air permeability, this being unsanitary.

(4) Switching on/off manipulation is troublesome. Moreover, such manipulation is likely to give the user an unnecessary impression that the user is being treated mechanically, which often fails to hold long.

SUMMARY OF THE INVENTION

A primary object of the present invention is to provide fiber for use as filling or wadding which has a voluminous and comfortable feeling, suppresses decomposition of proteins such as beta-keratin, prevents a foul odor inherent in such proteins, and has an excellent durability.

Another object of the present invention is to provide fiber for use as wadding which is capable of enhancing health as well as therapeutic treatment through an effect of far infrared ray.

Further objects and advantages of the present invention will become apparent to those skilled in the art from reading of the detailed description below.

In an attempt to achieve the above objects, after intensive studies, the present inventor has discovered that the aforementioned problems concerning the use of animal fibers and beddings utilizing far infrared rays can all be solved by affixing a far infrared rays radiating substance to the animal fiber together with a water repellent agent, and that the far infrared rays are effective for reducing the content of organic substances, a cause of an foul odor.

DETAILED DESCRIPTION OF THE INVENTION

Figure 1:
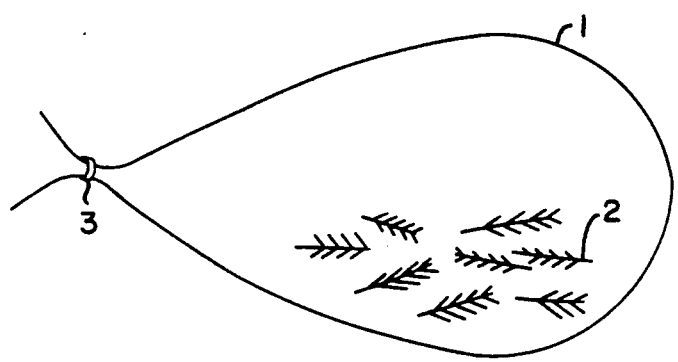
FIGS. 1 and 2 are diagrammatic views showing a method of experiment used in testing Example 1 of the present invention.

The first aspect of the present invention is to provide an animal fiber for use as wadding in which a far infrared rays radiating substance is affixed to the animal fiber together with water repellent agent, and the second aspect of the present invention is to provide an animal fiber in which a far infrared rays radiating substance is affixed to the animal fiber together with a water repellent agent, and then irradiated with far infrared rays.

Animal fibers in the present invention include, among others, feather, wool, mohair, alpaca, cashmere, hairs of camel and vicuna and silk and there is no particular limitation.

As the far infrared ray radiating substance, there is no particular limitation and the known ceramics of metal oxide type, and metals whose surface are deposited or flame sprayed with metal oxides preferably in the form of fine particles.

There is no particular limitation with regard to the water repellent agent in the present invention and any of the known water repellent agents such as silicon compounds, fluorine compounds, aluminum stearate and zirconium stearate are usable.

As to the method for affixing a far infrared radiating substance to an animal fiber together with a water repellent agent, there is no particular limitation and, for example, include (a) having fine particles of a far infrared radiating substance dispersed in a bath filled with a water repellent agent or said agent diluted with a suitable solvent and having the animal fiber dipped in the aforementioned dispersion, (b) having the aforementioned dispersion sprayed on the animal fiber, (c) sprinkling the far infrared ray radiating substance over the animal fiber with the water repellent agent affixed thereto. Those are followed by rinsing as necessary before drying.

By admixing the far infrared ray radiating substance with a far infrared ray reflecting substance e.g. aluminum it is possible to make the far infrared ray reflecting substance reflect the far infrared rays, thereby enabling still more effective utilization of far infrared rays.

According to the present invention, it is possible to irradiating the far infrared rays in the drying process or after drying, so that it is feasible to reduce the amount of organic substance to further enhance the deodorizing effect and to prevent propagation of molds and bacteria.

The animal fiber having affixed thereto the water repellent and also the far infrared radiating substance is wadded as filler into a bag-like container or clothes.

The beddings or clothes wadded with animal fibers having affixed to the surface thereof the water repellent agent have an improved fiber-to-fiber sliding property and an increased restoration from deformation under load, hence good bulkiness as well as good permeability is retained. The animal fibers of improved slidability move to where the wadding density is low in beddings or clothes to thereby keep the wadding density uniform. With the animal fibers of the present invention, the water repellent agent affixed to the surface thereof functions as a protective layer to repel sweat and waste matters, this being effective for prevention of decomposition of the animal fibers by the alkali contained in sweat or waste matters, and the fiber's durability is improved markedly. Furthermore, since the water repellent agent prevents propagation of molds, bacteria etc., mold or bacteria-induced foul smell is effectively prevented and beddings etc. can be kept clean.

Meanwhile, since animal fibers of the present invention have a far infrared radiating substance affixed to the surface thereof, the far infrared rays are radiated from the far infrared radiating substance which is exposed to the heat emitted from the human body, and it is possible to enjoy the action and effects unconsciously and naturally. Furthermore, since the far infrared rays radiating substance is affixed to the animal fiber, its intrinsic functions of touch, feel and voluminousness are by no means affected. Also, organic substances are eliminated by the far infrared rays, and hence the present invention is also effective for prevention of a foul odor and also for prevention of propagation of molds and bacteria.

Hereinafter, the present invention is explained in greater detail giving examples but, needless to say, the scope the present invention is by no means limited thereby.

EXAMPLE 1

(A) As shown in FIG. 1, a polyethylene bag (1) was filled with 50 g of feather (2), an inlet of the bag (1) was sealed by the use of a rubber band (3) and after 24 hours at the room temperature, a gas in the bag was let into FID (hydrogen flame ion detector) gas chromatography and analyzed under the conditions stated below. The gross area of the peak on the gas chromatograph was determined.

Gas chromatography: ShimadzuGC-4BMPF (FID)
Integrator: Shimadzu Chromatopack C-R3A
Column: PEG20M + PEG1500 (1:4)
Column temperature: 80° C.
Carrier gas: $N_2$ 50 ml/min., 1.2 kg/cm$^2$ G (B) 50 g of feather were dipped in a bath of silicone-based water repellent agent, the feather taken out of the bath was sprinkled with 1 g of far infrared radiating substance (ceramic) and then dried. Gas chromatographic analysis was carried out using the feather so treated in the same manner as described above in (A).

Figure 2:
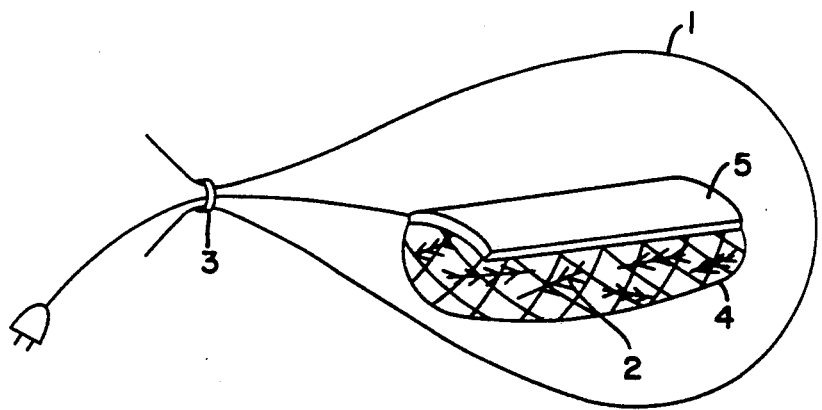

(C) As shown in FIG. 2, 50 g of feather (2) were wrapped up in a polyester net (4), to which a far infrared generator was provided, the whole was put in a polyethylene bag (1) with its inlet sealed with the rubber band (3), the far infrared generator (5) was operated for the pack of feather to be irradiated for 3 minutes and then in the manner described in (A) above it was left to stand for 24 hours and a gas in the bag was analyzed by means of gas chromatography.

(D) The feather having affixed thereto the water repellent agent and the far infrared radiating substance as described in (B) above was irradiated with far infrared rays in the way described above in (C) and a gas in the bag was analyzed by means of gas chromatography.

The results of the above (A)–(D) are shown in the Table 1 below.

TABLE 1

| Experiment | A | B | C | D |
| --- | --- | --- | --- | --- |
| Water repellent agent + Far infrared radiating substance | Not applied | Applied | Not applied | Applied |
| Far infrared radiating | Not applied | Not applied | Applied | Applied |
| Organic substance (counts) | 2,984 3.0 | 1,389 1.4 | 1,261 1.2 | 1,002 1.0 |

As seen from Table 1, the counts of organic substance in Examples (B)–(D) was far less than in Example (A) (blank).

According to the present invention, as mentioned above, by having a water repellent agent affixed to an animal fiber, marked numerous advantages are provided as below;

(1) Slidability is imparted to the animal fiber, this resulting in a good bulkiness and permeability because of no tangling of fibers and, furthermore, imparted is a good restorability from deformation under loading.

(2) The fibers treated with its improved slidability tend to move toward where the filling density is small, hence the fiber filling density in beddings or clothes becomes uniform.

(3) The affixed water repelling agent functioning as a protective layer repels sweat and waste matters, hence decomposition of fibers due to alkali contained in sweat and waste matters is prevented.

(4) The beddings and clothes are kept clean because sweat and waste matters are diffused through the interfiber spaces out of beddings or clothes.

(5) The water repellent agent prevents propagation of molds and bacteria, hence the beddings and clothes are kept clean of mold or bacteria-caused generation of a foul odor prevented.

(6) The fiber's durability is markedly improved through the cooperative actions set forth in the foregoing (1) to (5).

Furthermore, by having the far infrared radiating substance affixed thereto, the following advantages are further added;

(7) The health maintenance and enhancement and therapeutic effect of the far infrared rays can be enjoyed cheaply and simply without affecting any of the excellent functions of a wadding such as touch, comfortableness to sleep in bed and air permeability;

(8) Since the heat emitted from the human body is utilized, the heating cost is low and no power circuit is required, hence the structure is same as the conventional beddings and there is no fear of overheating or burn and the troublesome procedure of tuning on/off the switch is not necessary, hence the effect of far infrared radiating can be enjoyed under the same living pattern as hereinbefore; and (9) The far infrared radiating substance or far infrared radiation reduces an amount of organic substances, which eliminates an foul odor, and prevents propagation of molds and bacteria.

What is claimed is:

1. A material for use as filler in clothing and bedding comprising:

animal fibers having a surface thereof treated with a water repellant agent; and particles of a far infrared radiating substance adhered to said treated animal fiber surface.

2. A material as recited in claim 1, where said animal fibers are selected from the group consisting of feathers, wool, mohair, alpaca, cashmere, camel hair, vicuna hair and silk.

3. A material as recited in claim 1 or 2, wherein said far infrared radiating substance comprises fine particles of a metal oxide ceramic.

4. A material as recited in claim 1 or 2 wherein said water repellant agent comprises a material selected from the group consisting of silicon compounds, fluorine compounds, aluminum stearate and zirconium stearate.

5. A material as recited in claim 3, wherein said treated animal fiber surface has adhered thereto an infrared ray reflecting substance admixed with said infrared radiating substance.

6. A material as recited in claim 5 wherein said reflecting substance is aluminum.

* * * * *